United States Patent [19]
Gysler et al.

[11] Patent Number: 5,827,724
[45] Date of Patent: *Oct. 27, 1998

[54] BAKER'S YEASTS HAVING A LOW TEMPERATURE INACTIVATION PROPERTY

[75] Inventors: Christof Gysler; Herbert Hottinger, both of Blonay; Peter Niederberger, Epalinges, all of Switzerland

[73] Assignee: Nestec S.A., Vevey, Switzerland

[ * ] Notice: The term of this patent shall not extend beyond the expiration date of Pat. No. 5,480,798.

[21] Appl. No.: 534,481

[22] Filed: Sep. 27, 1995

Related U.S. Application Data

[60] Continuation of Ser. No. 86,012, Jun. 30, 1993, Pat. No. 5,480,798, which is a division of Ser. No. 777,029, Oct. 16, 1991, abandoned.

[30]     Foreign Application Priority Data

Nov. 9, 1990 [CH] Switzerland .............................. 565/90

[51] Int. Cl.[6] ..................................... C12N 1/18
[52] U.S. Cl. .................... 435/255.2; 435/172.1; 426/62
[58] Field of Search .............................. 435/255.2, 255.1, 435/172.1; 426/62

[56]         References Cited

U.S. PATENT DOCUMENTS

| | | |
|---|---|---|
| 4,318,929 | 3/1982 | Clement et al. . |
| 4,341,871 | 7/1982 | Langejan et al. . |
| 4,547,374 | 10/1985 | Nakatomi et al. . |
| 4,643,901 | 2/1987 | Jacobson et al. . |
| 5,514,386 | 5/1996 | Domingues . |

FOREIGN PATENT DOCUMENTS 61-195637  8/1986  Japan .

OTHER PUBLICATIONS

Hara, et al., The Breeding of Cryophilic Killer Wine Yeasts. Agric. Biol. Chem. 45(6) pp. 1327–1334 (1981).
Spencer, et al., Genetic Manipulation of non–conventional yeasts by conventional and non–conventional Methods. J. Basic Microbiol. 28:5, pp. 321–333 (1988).
Show, Genetic Improvement of Wine Yeast, Yeast Genet. Fundam. Appl. Aspects. pp. 439–459, Spencer JFT, et al., (eds); Springer: Secaucus, NJ (1983).
Moir, et al., "Cold–Sensitive Cell–Division–Cycle Mutants of Yeast: Isolation, Properties and Pseudoreversion Studies." Genetics, vol. 100, pp. 547–563 (1982) (Moir I).
Moir, et al., "Determination of the Order of Gene Function in the Yeast Nuclear Division Pathway Using cs and ts Mutants", Genetics vol. 100 pp. 565–577 (1982) (Moir II).
Singh, et al., "Genetic Analysis of Mutations Affecting Growth of the *Saccharomyces Cerevisiae* at Low Temperature", Genetics, vol. 77, pp. 651–659 (1974); and.
Mortimer, *Yeast Genetic Stock Center Catalog*, Seventh Edition, 1991.

*Primary Examiner*—Irene Marx
*Attorney, Agent, or Firm*—Vogt & O'Donnell, LLP

[57]         ABSTRACT

Strains of *Saccharomyces cerevisiae* are substantially inactive at refrigeration temperatures of 3° C. to 9°–10° C. and recover their activity at temperatures of 13°–14° C.

2 Claims, 8 Drawing Sheets

BAKER'S YEASTS HAVING A LOW TEMPERATURE INACTIVATION PROPERTY

CROSS REFERENCE TO RELATED APPLICATIONS

This application is a continuation application of application Ser. No. 08/086,012, filed Jun. 30, 1993, and now U.S. Pat. No. 5,480,798, which was, in turn, a divisional application of application Ser. No. 07/777,029, filed Oct. 16, 1991 and abandoned.

BACKGROUND OF THE INVENTION

This invention relates to a process for the construction of a strain of baker's yeast having an lti property and a yeast strain constructed by this process.

There are various known processes for constructing strains of baker's yeast s which are based in particular on traditional genetics and which seek to provide these strains with particular properties useful in bakery.

For example, U.S. Pat. No. 4,547,374 describes the construction by selective hybridizations of a strain of the species Saccharomyces which is resistant to freezing and which may be used as a baker's yeast in the preparation of a bread dough intended to be frozen prior to fermentation and baking.

U.S. Pat. No. 4,341,871 describes hybrids of baker's yeast which can be dehydrated, even in pressed form, without excessive loss of their activity.

U.S. Pat. No. 4,643,901 describes pure strains of baker's yeast which are capable of fermenting and raising both sweetened and unsweetened doughs and which are obtained by hybridization by protoplasmic fusion of "petite" mutants.

Commercial bakery products intended to be stored in a refrigerator before fermentation and baking are also known. However, these products, such as rolls and croissants for example, contain a chemical raising agent.

SUMMARY OF THE INVENTION

The problem addressed by the present invention was to provide a process for constructing strains of baker's yeast and strains thus constructed which have an lti property, i.e. a property whereby they are inactive but survive under refrigeration (lti is the abbreviation for the English expression "low temperature inactive"), and which may be used as a baker's yeast in the production of bakery articles intended to be baked in an oven just before eating, for example after storage in a refrigerator, in a cold room or on a refrigerated shelf.

To this end, a first embodiment of the process according to the invention for constructing a strain of baker's yeast having an lti property is characterized in that a haploid strain of *Saccharomyces cerevisiae* is subjected to a mutagenic treatment, at least one mutant having an lti property is selected and is backcrossed at least once with a wild haploid strain of *Saccharomyces cerevisiae* having an opposite mating type, at least two backcross segregants having an lti property and opposite mating types are selected and are crossed at least once and a diploid strain thus obtained having a growth potential, an lti property and an ability to raise a dough is selected.

In the context of the invention, the expression "growth potential" is understood to be a capacity for cultivation in a high yield and with good productivity by an industrially workable culture process, more particularly by the traditional process for culturing baker's yeast known as the fed batch process (slow and progressive addition of a sugar solution to a yeast suspension with aeration to avoid the formation of alcohol during the production of biomass and to maximize the yield).

Similarly, the expression "an ability to raise a dough" is understood to be a capacity for very slowly transforming a dough at refrigeration temperature, for example by the very slow production of metabolites, such as $CO_2$ which can be absorbed by the dough and alcohol which can act as a preservative for the dough, the consequence of this very slow transformation being that the dough is capable of rising when it is placed directly in an oven, for example after having been stored in a refrigerator, in a cold room or on a refrigerated shelf.

In a second embodiment of the process according to the invention for constructing a strain of baking yeast having an lti property, a polyploid strain of *Saccharomyces cerevisiae* is optionally subjected to a mutagenic treatment and is then sporulated, at least one segregant having an lti property is selected and backcrossed at least once with another segregant of this strain having an opposite mating type, at least two backcross segregants having an lti property and opposite mating types are selected and crossed at least once and a polyploid strain thus obtained having a growth potential, an lti property and an ability to raise a dough is selected.

It has been possible by this process to construct strains of baker's yeast which have the property of being substantially inactive at the usual refrigeration temperatures, more particularly at temperatures of the order of 3° to 9° or 10° C., but of surviving at these temperatures and subsequently recovering their activity at a higher temperature, for example of the order of 13° to 14° C.

Accordingly, strains of baker's yeast of this type may be used instead of a chemical raising agent in the production of bakery articles intended to be baked in an oven just before eating after refrigeration. They may be used in particular in the production of preformed articles, such as for example rolls, croissants and pizza crusts or a dough to be kneaded in the kitchen, which after refrigeration and baking in an oven have organoleptic qualities comparable to those of the same articles freshly raised under the effect of a traditional commercial baker's yeast and baked in an oven.

Strains of the type in question may also be used as a temperature abuse indicator in food products to be stored under refrigeration.

DETAILED DESCRIPTION OF THE INVENTION

The process according to the invention may start out either from a haploid strain of *Saccharomyces cerevisiae*, such as those forming traditional laboratory baker's yeasts, or from a polyploid strain of *Saccharomyces cerevisiae*, such as those forming traditional commercial baker's yeasts for example.

Accordingly, in the first above-described embodiment of the process according to the invention which starts out from a haploid strain of *Saccharomyces cerevisiae*, this strain is subjected to a mutagenic treatment. To this end, cells of this strain may be grown in a YPD medium containing, for example, 2% glucose, 1% yeast extract and 2% peptone and the cells may be treated with a mutagenic agent such as, for example, ethyl methanesulfonate (EMS) or ICR-170.

Several mutants having an lti property, more particularly a property of inactivity but survival at a temperature of the order of 9° or 10° C., are then preferably selected.

The mutant(s) selected are then backcrossed at least once with a wild haploid strain of *Saccharomyces cerevisiae* having an opposite mating type in order to avoid any unwanted mutations which the starting haploid strain may have at the outset or after the said mutagenic treatment and/or to retain if possible an lti property due to only a single mutation. If several backcross operations are carried out, at least one segregant having an lti property, more particularly a property of inactivity but survival at a temperature of approximately 9° or 10° C., may be selected between two successive operations and the segregant(s) thus selected may be subjected to the second of these two successive operations.

At least two backcross segregants having opposite mating types and an lti property, more particularly a property of inactivity but survival at a temperature of approximately 9° or 10° C., are then selected and are crossed at least once.

Finally, a diploid strain of *Saccharomyces cerevisiae* thus obtained having a growth potential, an lti property and an ability to raise a dough is selected. It is possible in this final stage to retain more severe and more complete selection criteria than those used in the preceding stages. More particularly, it is possible to subject the diploid strain(s) to a growth test in the traditional fed batch process for culturing baker's yeast .

The lti property may then be verified by subjecting the diploid strain(s) to a $CO_2$ production test in a maltose-containing nutrient medium, i.e. in a nutrient medium containing maltose as carbon source, as a function of temperature, for example every day between 3 and 7 d, and as a function of temperature, for example every degree between 3° and 14° C.

Finally, the ability of the strain to raise a dough may be verified by incorporation of the strain as sole raising agent in a pizza dough, for example by forming pizza crustswith this dough, storing them for a few days or even for a few weeks at refrigeration temperature and then baking them in an oven. This test may also be completed by verifying the $CO_2$ production of the strain in maltose-containing medium, for example at a temperature of approximately 20° to 30° C.

Accordingly, it is possible by this first embodiment of the process according to the invention to construct strains which have a remarkable lti property by virtue of which they may be used in the production of bakery articles intended to be baked in an oven just before eating after storage under refrigeration. More particularly, it is possible to construct strains of the baker's yeast *Saccharomyces cerevisiae* which have a growth potential in the fed batch process, an ability to raise a dough, a $CO_2$ production level of less than 20 ml per g pressed yeast after 7 d in maltose-containing medium refrigerated to 3°–10° C. and a $CO_2$ production level of at least 40 ml per g pressed yeast after 6 d in maltose-containing medium kept at a temperature of at least 14° C.

Among the various strains of *Saccharomyces cerevisiae* thus obtained, three were lodged by way of example at the National Collection of Industrial and Marine Bacteria Ltd. (NCIMB), P.O. Box 31, 135 Abbey Road, ABERDEEN AB9 8DG, Scotland (United Kingdom) under the Budapest Treaty on the 6th Nov. 1990 and have been given the Nos. NCIMB 40328, 40329 and 40330.

In the second embodiment of the process according to the invention, which starts out from a polyploid strain of *Saccharomyces cerevisiae*, this strain is thus optionally subjected to a mutagenic treatment. It has in effect been found that it was not always necessary to subject the strain to a mutagenic treatment because certain commercial baker's yeasts, for example, can initially show mutations capable of being detected in the course of the process according to the invention.

In cases where a polyploid strain is subjected to a mutagenic treatment, it is possible to this end to grow cells of this strain in a YPD medium containing for example, 2% glucose, 1% yeast extract and 2% peptone and the cells obtained may be treated with a mutagenic agent such as, for example, ethyl methanesulfonate (EMS) or ICR-70.

Accordingly, in this second embodiment of the process according to the invention, a polyploid strain of *Saccharomyces cerevisiae* is sporulated after having optionally been subjected to a mutagenic treatment. To sporulate this strain, cells thereof may be grown for 1 or 2 days on a so-called presporulation medium, such as a PSA medium containing 0.8% yeast extract, 0.3% peptone, 10% glucose and 2% agar. They may then be transferred and kept for 3 to 5 d on a sporulation medium, such as an SA medium containing 1% potassium acetate, 0.1% yeast extract, 0.05% glucose and 2% agar. The spores may then be isolated, for example by micromanipulation, and strains of reduced ploidy, in other words segregants, may be obtained from them, for example by germination on a YPD medium.

Several segregants of the said polyploid strain having an lti property, more particularly a property of inactivity but survival at a temperature of approximately 9°–10° C., are then preferably selected. The segregant(s) selected is/are then backcrossed at least once with another segregant of the polyploid strain which does not have the lti property, but an opposite mating type in order to avoid any unwanted mutations which the polyploid strain may have at the outset or after the optional mutagenic treatment and/or only to retain if possible an lti property due to a single mutation. If several backcross operations are carried out, at least one segregant having an lti property, more particularly a property of inactivity but survival at a temperature of approximately 9° to 10° C., may be selected between two successive operations and this or these segregant(s) may be subjected to the second of these two successive operations.

At least two backcross segregants having opposite mating types and an lti property, more particularly a property of inactivity but survival at a temperature of approximately 9° to 10° C., are then selected and are crossed at least once.

Finally, a polyploid strain of *Saccharomyces cerevisiae* thus obtained having a growth potential, an lti property and an ability to raise a dough is selected. To this end, the same selection criteria may be retained and the said polyploid strain(s) may be subjected to the same tests as described above in the final stage of the first embodiment of the process according to the invention.

Accordingly, it is possible by this second embodiment of the process according to the invention to construct strains which have a remarkable lti property by virtue of which they may be used in the production of bakery articles intended to be baked in an oven just before eating after storage under refrigeration. More particularly, it is possible to construct strains of the baker's yeast *Saccharomyces cerevisiae* which have a growth potential in the fed batch process, an ability to raise a dough, a $CO_2$ production level of less than 30 ml per g pressed yeast after 7 d in maltose-containing medium refrigerated to 3°–9° C. and a $CO_2$ production level of at least 60 ml per g pressed yeast after 6 d in maltose-containing medium kept at a temperature of at least 13° C.

Among the various strains of *Saccharomyces cerevisiae* thus obtained, two were lodged by way of example at the National Collection of Industrial and Marine Bacteria Ltd. (NCIMB), P.O. Box 31, 135 Abbey Road, ABERDEEN AB9 8DG, Scotland (United Kingdom) under the Budapest Treaty on the 6th Nov. 1990 and have been given the Nos. NCIMB 40331 and 40332.

EXAMPLES

The process according to the invention and the strains obtained are illustrated by the following Examples, in which percentages and parts are by weight, unless otherwise indicated.

The Examples are preceded by a description of various tests and of the composition of the various media used, by a brief description of the various Figures of the accompanying drawings and by a Comparison Example.

TESTS

1. Growth test

To simulate a real growth test in the traditional fed batch process for culturing baker's yeast, a growth test was designed using various culture media containing non-fermentable carbon sources, such as lactic acid (S-lac medium), ethanol (S-EtOH 2% and S-EtOH 1% media) and glycerol (YPG medium).

The reasoning behind this test is that baker's yeast accumulates non-fermentable carbon-containing metabolites in response to a critical addition rate of a solution of a fermentable sugar, such as sucrose, in the course of the fed batch process. These metabolites have an inhibiting and toxic effect on the metabolism and on the respiration of the yeast. Strains having a high growth potential can accumulate these toxic carbon-containing metabolites at higher addition rates and are less sensitive to the accumulation of these metabolites than strains having a lower growth potential.

Figure 1:
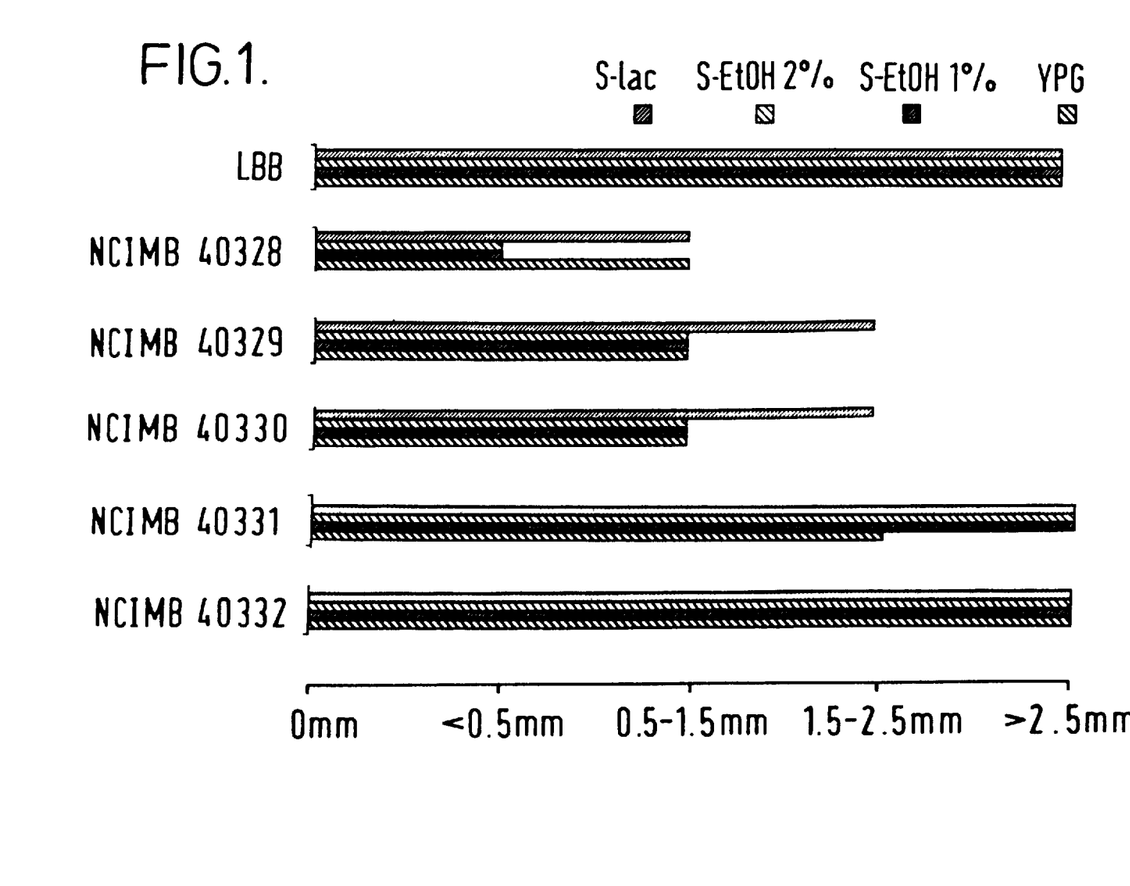
FIG. 1. is a linear representation of the size of the colonies obtained by growth on S-lac, S-EtOH 1% and 2% and YPG media of cells of the strains NCIMB 40328, 40329, 40330, 40331, 40332 and "levure boulangere bleue" (LBB, for comparison).

The results of this growth test are shown in FIG. 1 in terms of the dimensions which the colonies have after incubation of cells of a strain on plates of the said media for a period of 3 d at a temperature of 30° C. As illustrated in FIG. 1, the horizontal bands, which corresponds to each medium, stop at marks of 0; 0.5 mm; 0.5–1.5 mm; 1.5–2.5 mm; and 2.5 mm, which indicates a mean observed size of the colonies.

2. $CO_2$ production test

This test is carried out in a specially designed apparatus comprising a temperature gradient block, for example having cells at various temperatures into which the lower end of fermentation tubes may be introduced. These tubes have a closed and graduated upper end and an expansion flask connected to one side. The $CO_2$ produced by the yeast accumulates in the upper graduated end of each tube, the culture medium displaced by the accumulation of gas being able to pass into the expansion flask.

To carry out this test, 2 ml of an overnight culture in YPD medium of the strain to be tested is inoculated into 200 ml of a first medium containing 0.67% of a nitrogen base without amino acids, such as the product marketed by the Difco company under the name "yeast nitrogen base w/o amino acids", for example, 0.5% yeast extract, 2% sucrose, 1% sodium succinate and concentrated hydrochloric acid to adjust the pH to 4.5 in a 500 ml flask. The whole is incubated with stirring for 24 h at 30° C.

The cells are separated by centrifugation at 6,000 g/20° C. for 5 minutes and are then suspended in 200 ml of a second medium containing 0.67% of a nitrogen base without amino acids, 0.3% yeast extract and 0.3% sucrose, 1% sodium succinate and concentrated hydrochloric acid to adjust the pH to 4.5 in a 500 ml flask. The whole is incubated for 24 h at 30° C.

The cells are separated by centrifugation at 6,000 g/4° C. for 5 minutes and the residue of yeast cells obtained is washed twice with 50 ml distilled water.

The cells are suspended in 10 ml distilled water and are transferred to 15 ml graduated and preweighed polypropylene tubes. They are centrifuged at 3,000 g/4° C. for 10 minutes. The tubes are drained, the yeast residues are weighed and are suspended in a quantity of 0.61 g yeast residue equivalent to 0.5 g pressed yeast having a dry matter content of approximately 27% per ml in a third medium containing 0.67% nitrogen base without amino acids, 2% maltose, 1% sodium succinate and concentrated hydrochloric acid to adjust the pH to 4.5. Quantities of 0.5 ml (for temperatures of $\geq 10°$ C.) or 1 ml (for temperatures of <10° C.) are introduced into fermentation tubes of the type described above which have each been filled with 50 ml of the third medium, in other words the maltose-containing medium, and cooled to 4° C.

The fermentation tubes are incubated at the desired temperatures in the temperature gradient block described above. The production of $CO_2$ is recorded at selected intervals after the tubes have been immersed for a few seconds in a sonication bath to release $CO_2$ bubbles retained in the liquid medium.

3. Dough raising test

A dough is prepared by mixing 30 parts water, 60 parts white soft wheat flour, 1.4 parts sodium chloride and 7.6 parts peanut oil. The strain to be tested is incorporated in the flour in a quantity of 1 part pressed yeast. 20 cm diameter and 0.5 cm thick pizza crusts are then formed from the dough and are stored for 21 d at 8° C. in a sealed plastic wrapping.

The pizza crusts are then removed from their wrapping and baked in an oven for 15 minutes at 180° C.

The test is considered to have been passed if the pizza crusts have a thickness of approximately 2 cm and organoleptic qualities, namely a taste and texture, comparable with those of analogous pizza crusts prepared with a dough freshly raised under the effect of a traditional commercial baker's yeast.

MEDIA

YPD
   Glucose 2%
   Yeast extract 1%
   Peptone 2%

PSA
   Glucose 10%
   Yeast extract 0.8%
   Peptone 0.3%
   Agar 2%

SA
   Glucose 0.05%
   Yeast extract 0.1%
   Potassium acetate 1%
   Agar 2%

S-lac
   0.67% Nitrogen base without amino acids
   0.5% Lactic acid
   2% Agar S-EtOH 1% or 2%
   0.67% Nitrogen base without amino acids
   1% or 2% Ethanol
   2% Agar YPG
   Glycerol 2%
   Yeast extract 1%
   Peptone 2%

BRIEF DESCRIPTION OF THE DRAWINGS

Each of FIGS. 2 through 7 is, respectively, a three-dimensional representation of the $CO_2$ production level in maltose medium as a function of the temperature and time for the strains NCIMB 40328 (FIG. 2), NCIMB 40329 (FIG. 3), NCIMB 40330 (FIG. 4), NCIMB 40331 (FIG. 5), NCIMB 40332 (FIG. 6) and "levure boulangere bleue" (LBB for comparison, FIG. 7).

COMPARISON EXAMPLE

By way of comparison, a strain of commercial baker's yeast, namely a strain forming the baker's yeast marketed by the Fould Springer company under the name "levure boulangere bleue" (LBB), is subjected to the same tests as those used above to select the said diploid and polyploid strains having a growth potential, an lti property and an ability to raise a dough, i.e. to tests 1 to 3 described above.

The results of the comparative growth test presented in FIG. 1 show as expected that the LBB strain has a very good growth potential in the traditional fed batch process for culturing baker's yeast .

Figure 7:
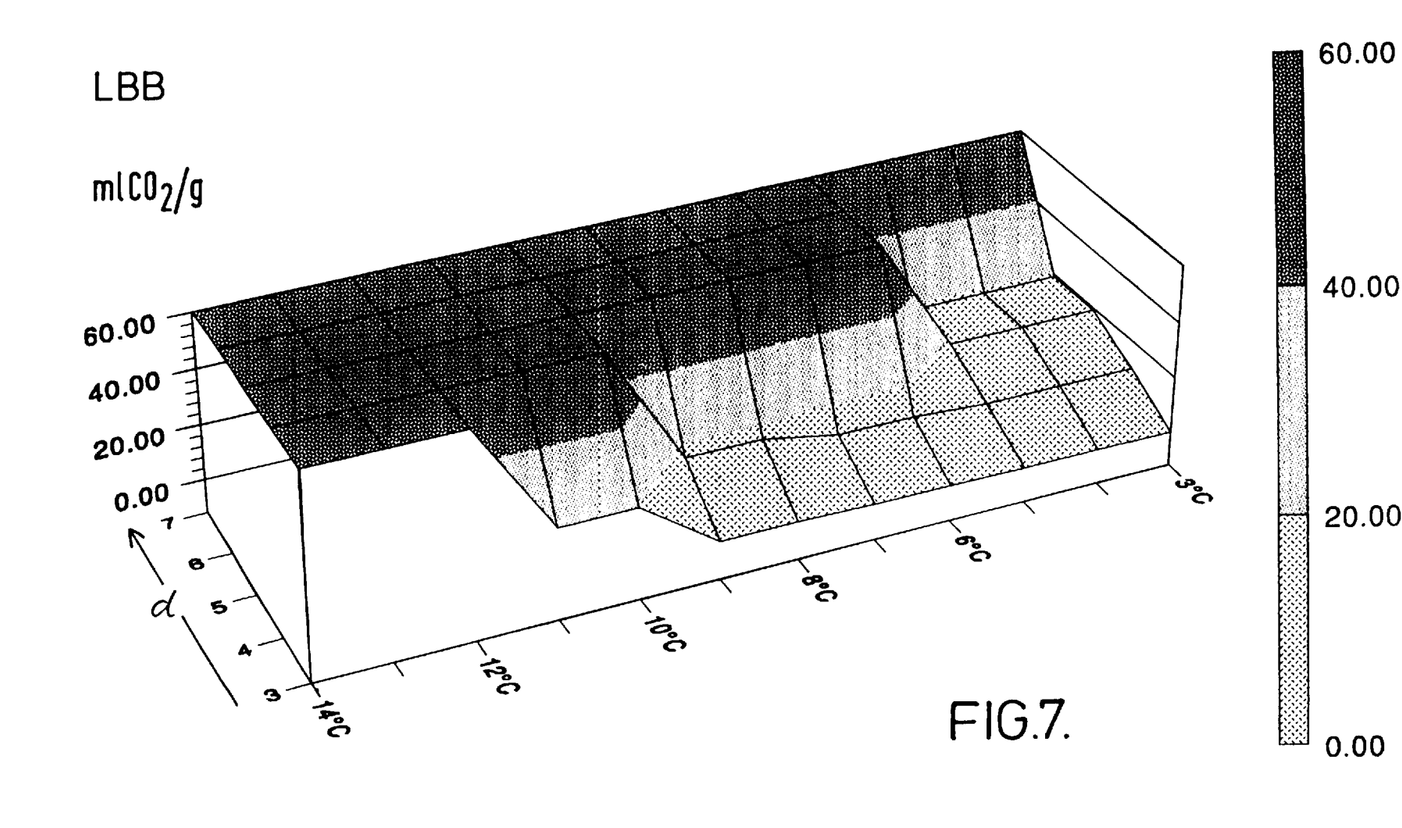

The results of the comparative $CO_2$ production test are presented in FIG. 7 where it can be seen that the production of $CO_2$ in maltose medium exceeds 40 ml per g pressed yeast after 6–7 d at 3°–5° C., after 5–6 d at 5°–9° C. and after 3–4 d at 10° C.

Figure 8:
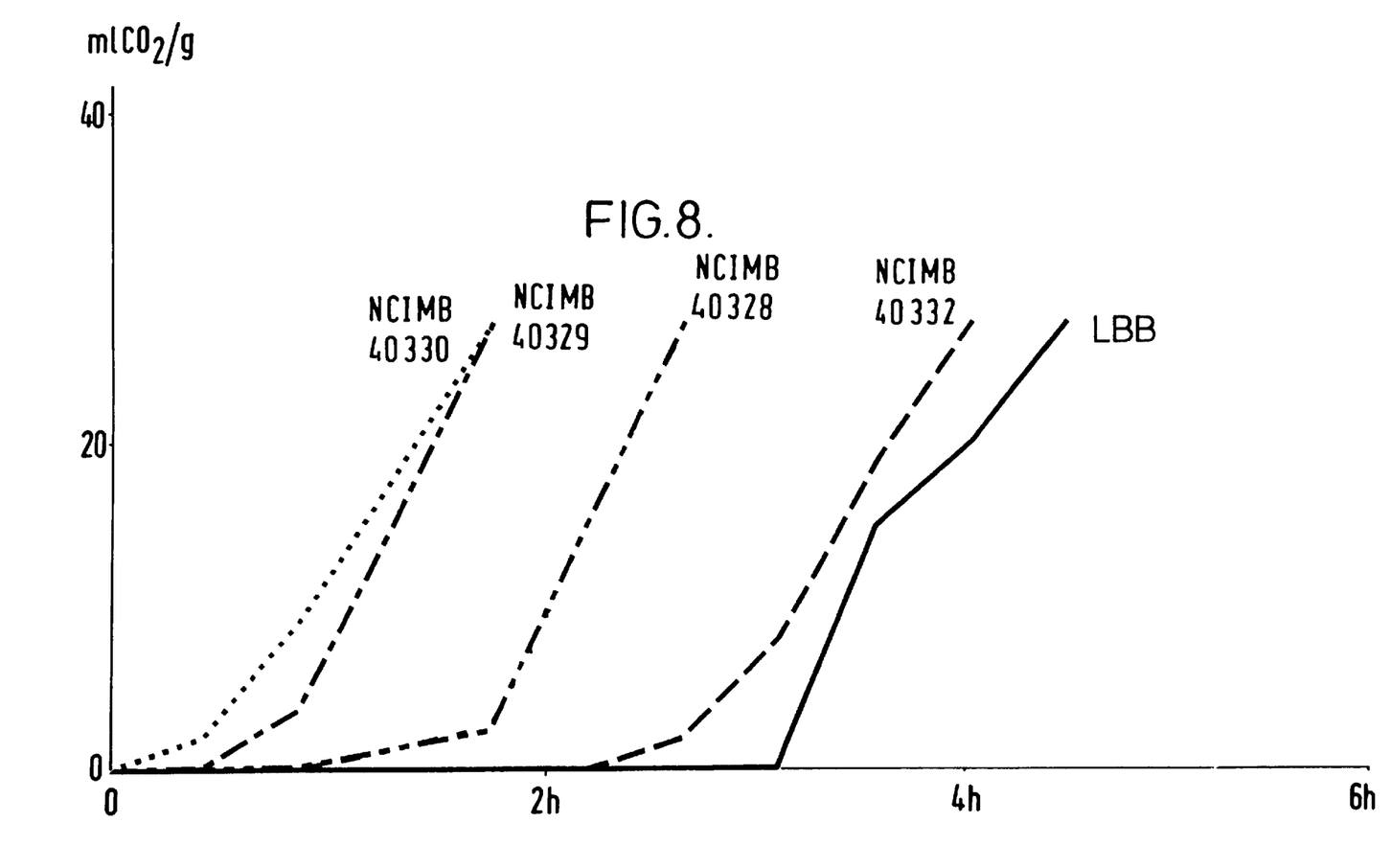
FIG. 8 is a two-dimensional representation of the $CO_2$ production level in maltose medium at 30° C. as a function of time for the strains NCIMB 40328, 40329, 40330 and 40332 and "levure boulangere bleue" (LBB for comparison).

It can also be seen from FIG. 8 that the $CO_2$ production in maltose medium of the LBB strain rapidly exceeds 20 ml per g pressed yeast after approx. 4 h at 30° C.

The results of the comparison test for raising a dough show that the LBB strain does not lend itself to refrigerated storage before baking in an oven. The sealed plastic wrapping in which a pizza crust obtained using the LBB strain is wrapped inflates like a balloon after 1 d at 8° C.

By contrast, it can be seen that there is hardly any discernible difference in quality between the pizza crusts obtained using strains constructed by the process according to the invention and subjected to the above dough raising test on the one hand and the pizza crusts obtained using the LBB strain and subjected to the same test without the refrigerated storage phase.

Example 1

The starting strain is a haploid strain of *Saccharomyces cerevisiae*, such as those forming traditional laboratory baker's yeasts, more particularly a strain having the genotype MATa arg4-17 his4-38 lys1-1 met8-1 trp1-1 mal, which was lodged under the Budapest Treaty on the 06.11.90 at the National Collection of Industrial and Marine Bacteria Ltd. (NCIMB), P.O. Box 31, 135 Abbey Road, ABERDEEN AB9 8DG, Scotland (United Kingdom), where it has been given the No. NCIMB 40333.

This strain is subjected to a mutagenic treatment with EMS. To this end, cells of this strain are grown in 5 ml of YPD culture medium up to the stationary phase, washed once with a 100 mM potassium phosphate buffer at pH 7.0 and then suspended in the same buffer in a quantity of $10^8$ cells/ml.

3% by volume EMS is added to the suspension which is then left to react for 1 h at 30° C. with vigorous stirring. The treatment is terminated by dilution of the suspension in 10 times its volume of a 5% solution of sodium thiosulfate. The cells are then distributed over solid YPD medium and are cultured thereon for 2 d at 30° C. They are then redistributed over solid YPD medium and cultured thereon for 3 weeks at 10° C. to test their lti property.

Some stable mutants having the property of inactivity but survival at that temperature are then selected.

One of these mutants having a mating type MATa is then backcrossed with a wild haploid strain of *Saccharomyces cerevisiae* such as, for example, the strain GRF18 having the genotype MATα can1 his3-11,15 leu2-3,112, which is well known to the expert (cf. G. R, Fink, Whitehead Institute, Nine Cambridge Center, Cambridge, Mass. 01 142, USA).

A segregant of this backcross having a pronounced lti property at 10° C. and the genotype MATa lys1 his3/4 trp1 mal is then selected.

This segregant is backcrossed with the same wild strain as that used for the backcross of a mutant of the starting strain.

Two segregants of this backcross showing a pronounced lti property at 10° C. and each having the genotype MATα leu2 his3/4 mal are then selected.

Each of these two segregants is backcrossed with a wild haploid strain of *Saccharomyces cerevisiae* having at least one MAL gene such as, for example, the strain 1403-7A which is well known to the expert (cf. Yeast Genetics Stock Center, 6th Edition of the Catalog by Robert Mortimer, Department of Biophysics and Medical Physics, University of California, Berkeley, Calif. 94720, USA).

A segregant of each of these backcrosses each with a very pronounced lti property at 10° C. is then selected, one having a genotype MATa MAL and the other a genotype MATα leu2 MAL.

These two segregants are crossed and various diploid strains of *Saccharomyces cerevisiae* produced by this crossing, which have a growth potential, an lti property and an ability to raise a dough, are selected.

Among the various strains thus obtained, the above-mentioned strain NCIMB 40328 has been lodged by way of example. This strain has a relatively modest growth potential in the traditional fed batch process for culturing baker's yeast, as can be seen from FIG. 1 which illustrates the results obtained in the above growth test.

However, it shows a high capacity for fermenting a dough because it easily passes the corresponding test described above.

Figure 2:
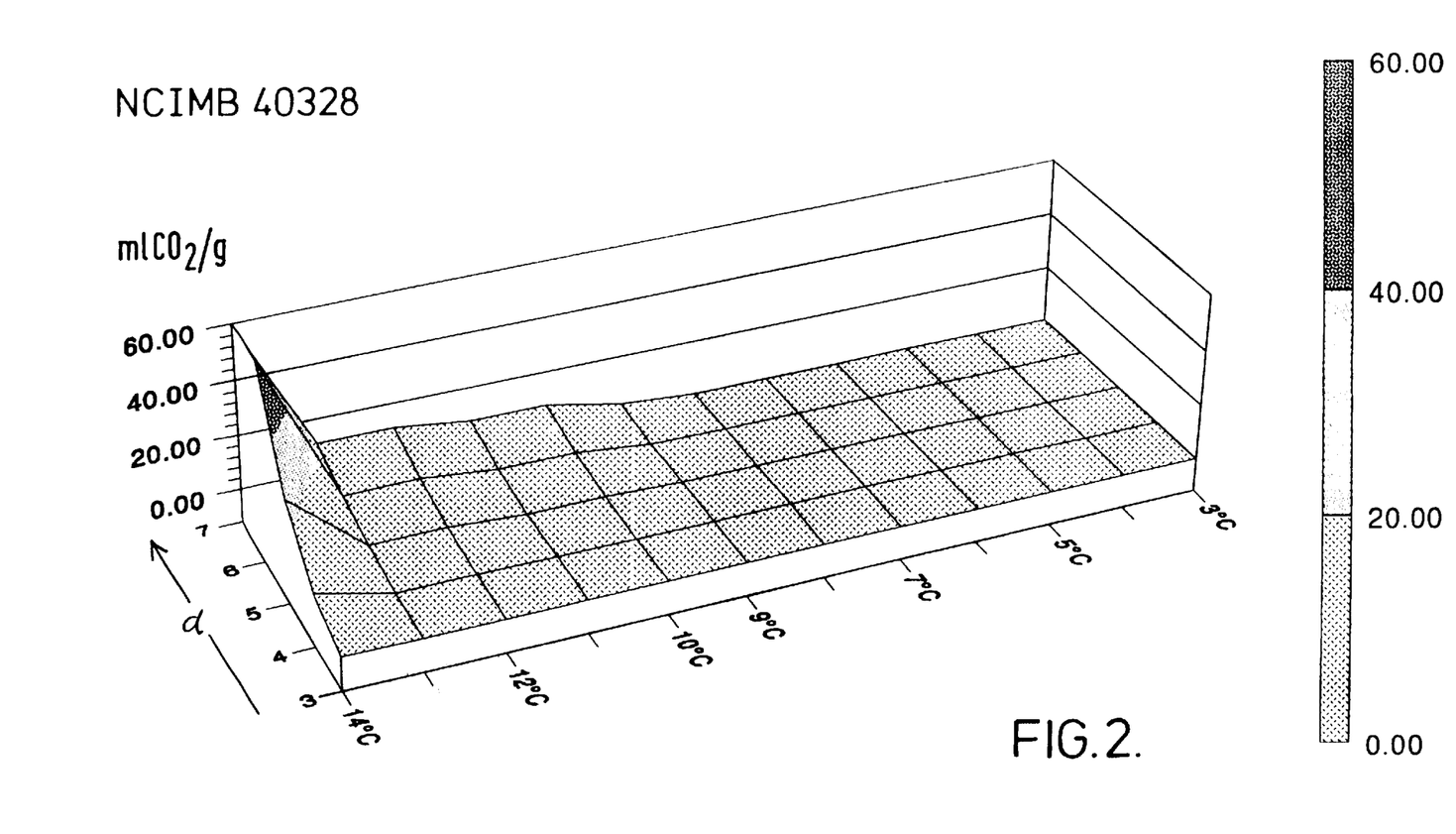

Finally, it has a prounced lti property, as can be seen from FIG. 2 which is a three dimensional diagram showing its $CO_2$ production level as a function of the fermentation temperature and time in maltose medium, as determined by the $CO_2$ production test described in detail in the foregoing. It can be seen that it is substantially inactive between 3° and 10° C. for at least about 1 week, but survives and is capable of returning to significant activity after about 6 to 7 d at approximately 13° to 14° C. More particularly, it can be seen that its $CO_2$ production level is still around zero after 7 d between 3° and 8° C. and that it only rises to approximately 8 ml per g pressed yeast after 7 d at 10° C. By contrast, its $CO_2$ production level in maltose medium increases to more than 40 ml/g after 6 d at 13° to 14° C.

It can also be seen from FIG. 8 that its $CO_2$ production level in maltose medium increases rapidly to more than 20 ml/g after approximately 2 h at 30° C.

In addition, the strain NCIMB 40328 shows the following characteristics:

Morphology

Elliptical cells. Certain cells increase in size and form a pseudomycelium.

Fermentation of sugars:

The strain is capable of fermenting sucrose, maltose and glucose.

Example 2

The starting strain used and the procedure are both as described in Example 1 up to selection of the two backcross segregants having a pronounced lti property at 10° C. and the genotype MATα leu2 his3/4 mal.

One of these two segregants is backcrossed with a wild haploid strain of Saccharomyces cerevisiae such as, for example, the strain X2180-1A having the genotype MATa CUP1 SUC2 gal2 mal mel which is well known to the expert (cf. Yeast Genetics Stock Center, 6th Edition of the Catalog).

A segregant of this backcross having a pronounced lti property at 10° C. and the genotype MATα his3/4 leu2 mal is selected.

This segregant is backcrossed with the same strain X2180-1A as above to eliminate the auxotrophic mutations his3/4 and leu2.

A segregant of this backcross having the genotype MATα mal and a significant lti property at 10° C. due to a single mutation, in other words having a perfect 2:2 segregation in regard to the lti property, is selected.

This segregant is backcrossed with a wild haploid strain of Saccharomyces cerevisiae having at least one MAL gene such as, for example, the strain 1403-7A which is well known to the expert (cf. Yeast Genetics Stock Center, 6th Edition of the Catalog).

On the one hand, one segregant of this backcross having a pronounced lti property at 10° C. and the genotype MATα MAL and, on the other hand, two segregants of this backcross respectively showing pronounced and very pronounced lti properties at 10° C., each with the phenotype MATa ura3 mal, are selected.

Each of these two last segregants is crossed with the first and various diploid strains of Saccharomyces cerevisiae produced by these two crossings, which have a growth potential, an lti property and an ability to raise a dough, are selected.

Among the various strains thus obtained, the abovementioned strains NCIMB 40329 and NCIMB 40330 each produced by one of these two crossings having been lodged by way of example. These two strains have a relatively good growth potential in the traditional fed batch process for culturing baker's yeast, as can be seen from FIG. 1.

They also have a good ability to raise a dough because they easily pass the corresponding test described above.

Figure 3:
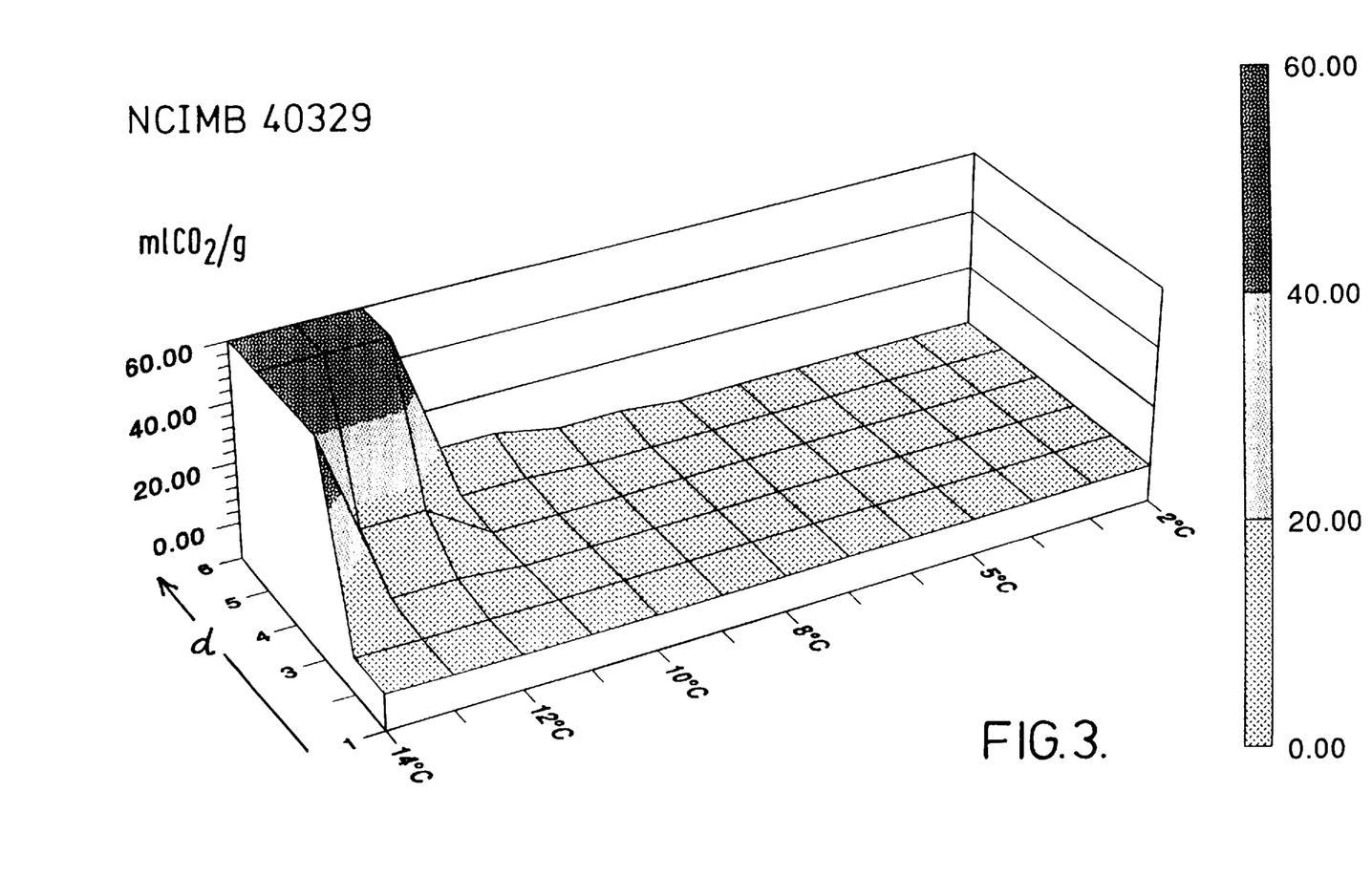
Figure 4:
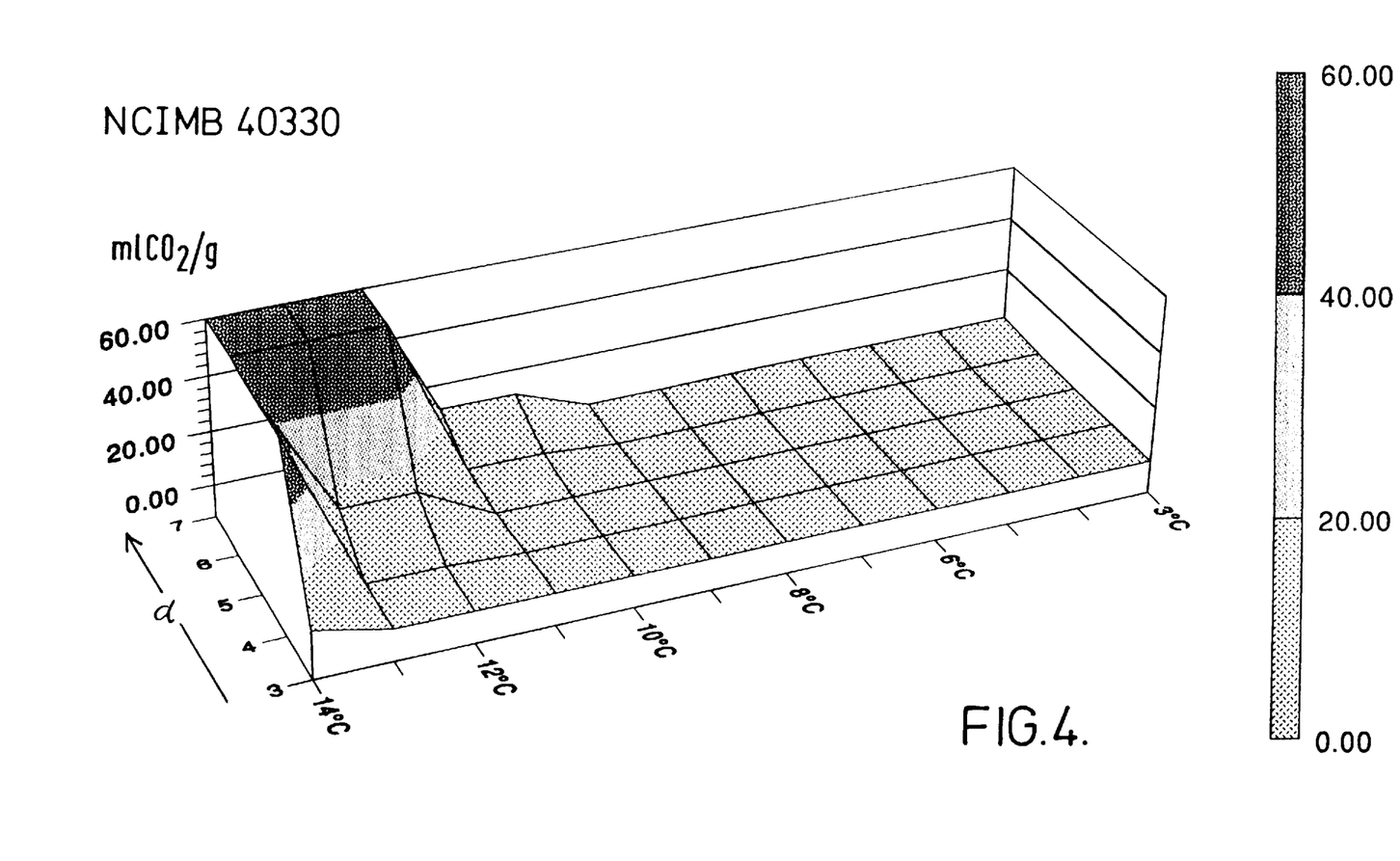

Finally, they have a marked lti property. Thus, it can be seen from FIGS. 3 and 4 that they are substantially inactive in maltose medium between 3° and 10° C. for at least about 1 week, but survive and are capable of returning to significant activity after about 5 to 7 d at approximately 11° to 14° C. More particularly, it can be seen that their $CO_2$ production level is still around zero after 7 d between 3° and 9° C. and that it only rises to approximately 12 ml per g pressed yeast after 7 d at 10° C. By contrast, their $CO_2$ production level increases to more than 40 ml/g after 6 d at 12° to 14° C.

It can also be seen from FIG. 8 that their $CO_2$ production level in maltose medium increases rapidly to more than 20 ml/g after approximately 1.5 h at 30° C.

In addition, these strains show the following characteristics:

NCIMB 40329

Morphology:

Elliptical cells. Cells of relatively homogeneous size.

Fermentation of sugars:

Capable of fermenting sucrose, maltose and glucose.

NCIMB 40330

Morphology:

Elliptical cells. Cells of relatively homogeneous size.

Fermentation of sugars:

Capable of fermenting sucrose, maltose and glucose.

Example 3

The starting strain is a commercial polyploid strain of Saccharomyces cerevisiae such as that forming the baker's yeast marketed by the Fould Springer company under the name "levure boulangere bleue", of which the cells contain three to four times more DNA than the cells of a haploid strain of Saccharomyces cerevisiae.

To sporulate this strain, its cells are grown on a PSA presporulation medium for 2 d at 30° C. They are then transferred to an SA sporulation medium where they are kept for 4 d at 30° C.

Spores are then isolated and germinated on a YPD culture medium to obtain strains, i.e. segregants, having reduced ploidy.

One of these segregants having a very pronounced lti property at 10° C. and, in addition, the mating type MATα is selected.

This segregant is backcrossed with another of the segregants of reduced ploidy which does not show an lti property, but does have the mating type MATa.

Several segregants of this backcross which have a very pronounced lti property at 10° C. and one mating type are selected.

Segregants having opposite mating types are crossed several times and various polyploid strains of Saccharomyces cerevisiae produced by these crossings, which have a growth potential, an lti property and an ability to raise a dough, are selected.

Among the various strains thus obtained, the abovementioned strains NCIMB 40331 and NCIMB 40332 have been lodged by way of Example. More particularly, these two strains have a very good growth potential in the traditional fed batch process for culturing baker's yeast, as can be seen from FIG. 1.

They also have a good ability to raise a dough because they easily pass the corresponding test described above.

Figure 5:
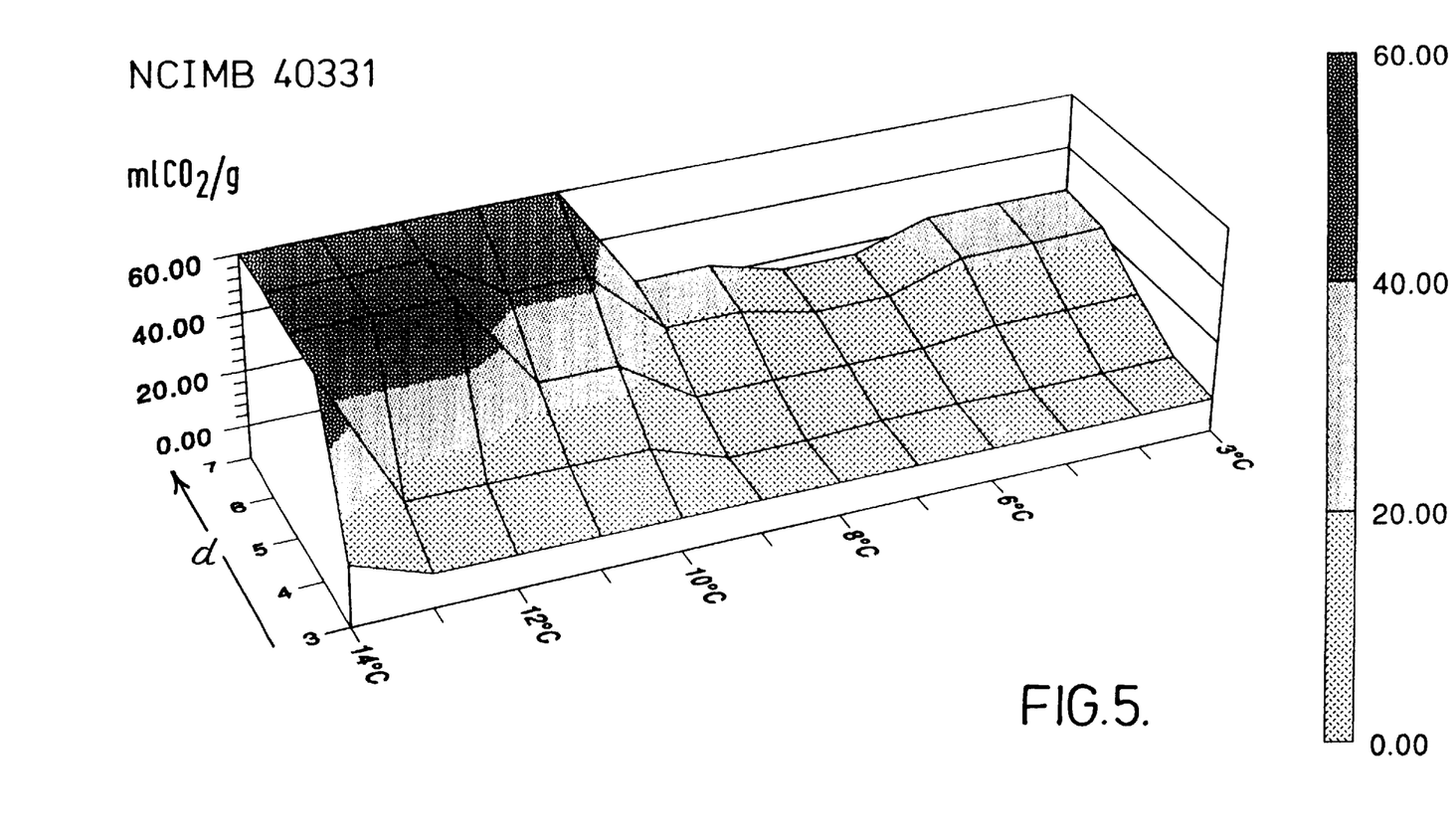
Figure 6:
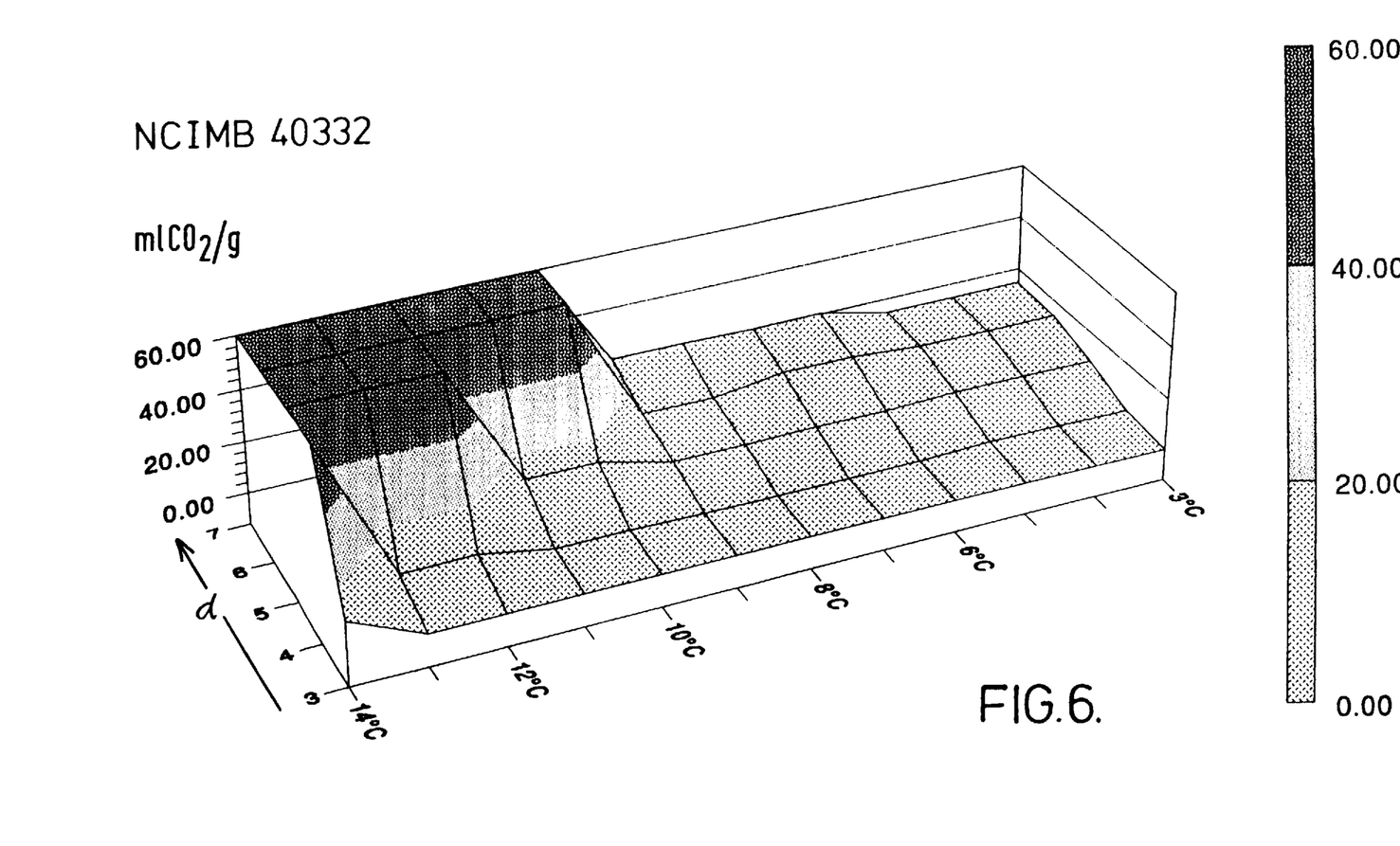

Finally, they have a pronounced lti property. Thus, it can be seen from FIGS. 5 and 6 that they are substantially inactive in maltose medium between 3° and 9° C. for at least 4 to 5 d, but survive and are capable of returning to significant activity after about 5 to 7 d at approximately 10° to 13° C. More particularly, it can be seen that their $CO_2$ production level is still around zero after 5 d between 3° and 9° C. and that it only rises to approximately 20 to 25 ml per g pressed yeast after 7 d at 3° to 9° C. By contrast, their $CO_2$ production level increases to more than 60 ml/g after 5 d at 12° to 14° C.

It can also be seen from FIG. 8 that the $CO_2$ production level of the strain NCIMB 40332 in maltose medium increases rapidly to more than 20 ml/g after approximately 4 h at 30° C.

In addition, these strains have the following characteristics:

NCIMB 40331
morphology:
Round cells. Cells of homogeneous size.
Fermentation of sugars:
Capable of fermenting sucrose, maltose and glucose.

NCIMB 40332
Morphology:
Round cells. Cells of homogeneous size.
Fermentation of sugars:
Capable of fermenting sucrose, maltose and glucose.

We claim:

1. An isolated diploid strain of *Saccharomyces cerevisiae* which grows on a plate in a medium comprising, by weight, 2% glycerol, 1% yeast extract and 2% peptone, and forms a colony size greater than 0.5 mm after 3 days of culture at 30° C.; which raises a 20 cm diameter/0.5 cm thick pizza dough stored in a sealed plastic wrapping for 21 days at 8° C. to an about 2 cm thick pizza crust when baked at 180° C. for 15 minutes; which produces $CO_2$ at a level of less than 20 ml/g pressed yeast after 7 days in a medium containing 2% by weight maltose refrigerated at from 3° C. to 10° C.; and which produces $CO_2$ at a level of at least 40 ml/g pressed yeast after 6 days in a medium containing 2% by weight maltose kept at a temperature of at least 14° C.

2. An isolated polyploid strain of *Saccharomyces cerevisiae* which grows on a plate in a medium comprising, by weight, 2% glycerol, 1% yeast extract and 2% peptone, and forms a colony size greater than 0.5 mm after 3 days of culture at 30° C.; which raises a 20 cm diameter/0.5 cm thick pizza dough stored in a sealed plastic wrapping for 21 days at 8° C. to an about 2 cm thick pizza crust when baked at 180° C. for 15 minutes; which produces $CO_2$ at a level of less than 30 ml/g pressed yeast after 7 days in a medium containing 2% by weight maltose refrigerated at from 3° C. to 9° C.; and which produces $CO_2$ at a level of at least 60 ml/g pressed yeast after 6 days in a medium containing 2% by weight maltose kept at a temperature of at least 13° C.

* * * * *